United States Patent [19]

Perron et al.

[11] Patent Number: 4,927,957

[45] Date of Patent: May 22, 1990

[54] CATALYTIC DIMERIZATION OF ALKYL ACRYLATES

[75] Inventors: Robert Perron, Charly; Sylvain Mutez, Irigny, both of France

[73] Assignee: Rhone-Poulenc Chimie, Courbevoie, France

[21] Appl. No.: 234,154

[22] Filed: Aug. 19, 1988

[30] Foreign Application Priority Data

Aug. 19, 1987 [FR] France ................. 87 11831

[51] Int. Cl.$^5$ ............................................. C07C 67/465
[52] U.S. Cl. .................................... 560/202; 502/164; 560/190
[58] Field of Search ................... 560/202; 502/164

[56] References Cited

U.S. PATENT DOCUMENTS

| | | | |
|---|---|---|---|
| 4,451,665 | 5/1984 | Nugent | 560/202 |
| 4,485,256 | 11/1984 | McKinney | 560/202 |
| 4,504,674 | 3/1985 | McKinney | 560/202 |
| 4,547,323 | 10/1985 | Carlson | 560/202 X R |
| 4,594,447 | 6/1986 | Wilke et al. | 560/202 |
| 4,638,084 | 1/1987 | Singelton | 560/202 |
| 4,786,623 | 11/1988 | Grenowillet et al. | 502/164 |

*Primary Examiner*—Werren B. Lone
*Assistant Examiner*—Vera C. Clarke
*Attorney, Agent, or Firm*—Burns, Doane, Swecker & Mathis

[57] ABSTRACT

Alkyl acrylates are catalytically dimerized, e.g., to produce alkyl diesters of dihydromuconic acid, in the presence of a catalytically effective amount of palladium, tetrafluoroboric acid and a hydrogenophosphonium tetrafluoroborate, and wherein the palladium concentration ranges from 0.1 to 3 mmol per mole of said at least one alkyl acrylate, the reaction temperature ranges from 70° to 150° C. and the hydrogenophosphonium tetrafluoroborate concentration is at least 6 mmol per mole of said at least one alkyl acrylate.

10 Claims, No Drawings

CATALYTIC DIMERIZATION OF ALKYL ACRYLATES

BACKGROUND OF THE INVENTION

1. Field of the Invention:

The present invention relates to an improved process for the catalytic dimerization of alkyl esters of acrylic acid to produce alkyl diesters of dihydromuconic acid.

2. Description of the Prior Art:

In European Patent Application No. 87/420,078.5 is described a process for the catalytic dimerization of a lower alkyl acrylate to produce alkyl diesters of dihydromuconic acid, by the reaction, at a temperature of from 50 to 250° C., of a lower alkyl acrylate in the presence of a catalytic system comprising palladium or a palladium compound, characterized in that the catalytic system is formed from at least:

(a) an unhalogenated source of palladium;

(b) a phosphorus (III) compound of the general formula (I):

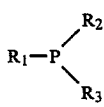

in which:

$R_1$, $R_2$ and $R_3$ denote, independently, an alkyl, cycloalkyl, aryl, alkoxy, cycloalkoxy or aryloxy radical, with the proviso that one of the radicals $R_1$, $R_2$ or $R_3$, in addition, may be a monovalent radical of the general formula (II):

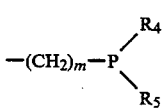

in which:

m is an integer ranging from 1 to 4, inclusive, and $R_4$ and $R_5$ denote, independently, an alkyl, cycloalkyl, aryl, alkoxy or aryloxy radical; and (c) at least one hydracid HY in which the associated anion $Y^-$ is non-coordinating in nature with respect to palladium ions The diesters thereby produced are intermediates which are useful, in particular in the preparation of alkyl adipates or even adipic acid.

The starting material is a lower alkyl acrylate, namely, one in which the alkyl residue contains from 1 to 8 carbon atoms; the size of the alkyl group is not critical and methyl acrylate and ethyl acrylate are preferably employed because of their greater availability. The alkyl group can contain substituents that do not interfere with the desired reaction.

Naturally, commercial products, not necessarily pure, can be used as the starting material.

The catalytic system according to this particular patent application is formed from at least one unhalogenated source of palladium. This palladium source, the precursor of the catalytically active entity, may be selected from among the various unhalogenated forms of palladium (0) or palladium (II). Among the forms of palladium (II) that are suitable for carrying out such process, exemplary are the salts of organic acids, such as palladium (II) acetate, palladium (II) formate, palladium (II) octanoate and palladium (II) ethylhexanoate; the salts of inorganic acids, such as palladium (II) nitrate; $\pi$-allyl complexes of palladium (II), such as ($\pi$-allyl)palladium diacetate; and palladium (II) acetyl acetonate.

The use of palladium (II) acetate or palladium (II) acetylacetonate is preferred, in particular because of their greater availability.

Among the sources of palladium (0) suitable for carrying out such process, exemplary are palladium black, palladium deposited on a support such as activated charcoal or silica gel, and complexes of palladium and a trialkyl- or triarylphosphine such as tetrakistriphenylphosphinepalladium.

Known useful such compounds are compounds of palladium (0) and dibenzylideneacetone, which correspond to the general formula (III) below:

$$Pd_x(dba)_y \qquad (III)$$

in which:

x is equal to 1 or 2;

dba denotes a dibenzylideneacetone ligand; and y is equal to 2 or 3, with y necessarily being equal to 3 when x equals 2.

These compounds are readily available. They may be easily prepared by the reduction of palladium chloride in the presence of dibenzylideneacetone (dba) according to any of the procedures described by Y. Ishii et al, Chem. Comm., p. 1065 (1970).

The complexes $Pd(dba)_2$, $Pd_2(dba)_3$ and $Pd(dba)_3$, and mixtures thereof, may thus be used.

Also in said patent application noted above, it is stated that a concentration of palladium in the reaction medium of at least 0.1 millimole per mole of acrylate appeared to be necessary in order to obtain a sufficient degree of conversion, and no advantage is said to be observed in exceeding the quantity of 3 millimoles of acrylate.

As regards the phosphorus (III) compound, it was specified in the '078.5 patent application that its quantity is generally such that the mole ratio P/Pd ranges from 1 to 15, with a mole ratio of from 1 to 3 being preferred.

As regards the hydracid HY, in which the associated anion $Y^-$ is non-coordinating in nature with respect to palladium ions, preferred was tetrafluoroboric acid, and it was stated that a quantity of acid such that the ratio $H^+/Pd$ ranges from 1 to 30, and preferably from 1 to 10, was required, it being possible to obtain good results with an $H^+/P$ radio on the order of approximately 2 to 5.

The preparation of the catalytic system at the time of use and its in situ preparation under the dimerization conditions were described, it being possible for the former to entail the prior synthesis of a hydrogenophosphonium salt such as tributylphosphonium tetrafluoroborate.

However, while the basic value of such a process is apparent, its development on an industrial scale prompts at least one of the following problems:

(1) insufficient activity of the catalytic system;

(2) lack of selectivity of the catalytic system which results, in particular, in the production of a significant proportion of heavy products; and (3) lack of stability of the palladium, which is capable of being deposited onto the walls of the reactor and which is capable of inducing substantial variations in activity with the passage of time.

These various problems become a matter of more particular concern when it is desired to carry out the process under conditions of temperature and palladium concentration which are compatible with industrial requirements, that is to say, a temperature of from 70° to 150° C. and a palladium concentration of from 0.1 to 3 mmol of palladium per mole of alkyl acrylate.

Cf. U.S. Pat. Nos. 3,792,101, 4,594,447 and 4,638,084, and FR-A-2,524,341.

SUMMARY OF THE INVENTION

Accordingly, a major object of the present invention is the provision of an improved process for the dimerization of alkyl acrylates which conspicuously ameliorates those disadvantages and drawbacks to date characterizing the state of this art.

Briefly, the present invention features a process for the dimerization of lower alkyl acrylates, comprising reacting at least one lower alkyl acrylate, in the presence of palladium, with tetrafluoroboric acid and a hydrogenophosphonium tetrafluoroborate, and wherein the palladium concentration ranges from 0.1 to 3 mmol per mole of alkyl acrylate, the reaction temperature ranges from 70° to 150° C. and the hydrogenophosphonium tetrafluoroborate concentration is greater than or equal to 6 mmol per mole of alkyl acrylate.

DETAILED DESCRIPTION OF THE PREFERRED EMBODIMENTS OF THE INVENTION

More particularly according to the present invention, by "lower alkyl acrylates" are intended compounds within the definition given above; methyl acrylate is more especially suitable for carrying out the present process as a result of its greater availability.

The palladium can be introduced in any one of the forms set forth hereinbefore, insofar as the compounds do not contain a halogen atom.

By "hydrogenophosphonium tetrafluoroborate" is intended the salt derived from the reaction between tetrafluoroboric acid and a phosphorus (III) compound corresponding to the general formula (I) given above.

This salt may be represented by the general formula (IV):

in which $R_1$, $R_2$ and $R_3$ are as defined above.

Specifically exemplary of $R_1$, $R_2$ and $R_3$ are:

(i) an alkyl radical containing at most 8 carbon atoms, such as methyl, ethyl, propyl, isopropyl, butyl, t-butyl and n-octyl radicals;

(ii) a cycloalkyl radical containing from 5 to 7 carbon atoms, such as a cyclohexyl or cycloheptyl radical;

(iii) an aryl radical containing from 6 to 12 carbon atoms, such as phenyl, p-tolyl, biphenylyl and naphthyl radicals;

(iv) an alkoxy radical containing at most 8 carbon atoms, such as methoxy and ethoxy radicals; and (v) an aryloxy radical containing from 6 to 12 carbon atoms, such as a phenoxy radical.

Tributylphosphonium tetrafluoroborate, tricyclohexylphosphonium tetrafluoroborate and dimethylphenylphosphonium tetrafluoroborate are especially suitable for carrying out the process according to the present invention.

The synthesis of the subject salts may be carried out at the time of use by adding, in a solvent medium, where appropriate, tetrafluoroboric acid (available in the form of an aqueous solution or in the form of complexes with ethers, such as ethyl ether and methyl ether) to the corresponding phosphorus (III) compound. The solvent for this synthesis can be the substrate employed in the dimerization reaction. Of course, this synthesis can also be carried out in the presence of palladium or compounds thereof.

The palladium concentration ranges from 0.1 to 3 mmol per mole of alkyl acrylate. To satisfactorily carry out the process according to this invention, it advantageously ranges from 0.2 to 1.5 mmol per mole of alkyl acrylate.

The temperature of the dimerization reaction ranges from 70° to 150° C. Advantageously it ranges from 90° to 130° C.

The hydrogenophosphonium tetrafluoroborate concentration is greater than 6 mmol per mole of alkyl acrylate. No particular advantage is observed in exceeding a concentration on the order of 200 mmol per mole of alkyl acrylate. This concentration will advantageously range from 10 to 100.

Nonetheless, to satisfactorily carry out the process according to the invention, the minimum threshold value of this concentration will increase as the selected reaction temperature increases.

The process according to the invention is also carried out in the presence of fluoroboric acid. The quantity of acid to be employed will generally range from 0.5 to 50 mmol per mole of alkyl acrylate, and preferably from 2 to 15 mmol per mole of alkyl acrylate. The reaction time (or residence time) generally ranges from 10 minutes to 8 hours.

The reaction products can then be recovered by distillation after neutralization of the reaction medium and, where appropriate, a first distillation to effect the removal of the dissolving intermediary when this is necessary.

In order to further illustrate the present invention and the advantages thereof, the following specific examples are given, it being understood that same are intended only as illustrative and in nowise limitative. In said examples to follow, the following conventions are employed:

Bu=n-butyl,

MA=methyl acrylate,

Pd (acac)$_2$ =palladium acetylacetonate,

[HBF$_4$]=concentration of excess tetrafluoroboric acid, t=duration of the experiment at the working temperature and at the time of withdrawing a sample, RY=number of moles of the product in question for 100 moles of methyl acrylate introduced, 2-MEG=methyl 2-methyleneglutarate, DHM=Δ2- and Δ3-dihydromuconate, Soluble [Pd]=concentration of soluble palladium in mmol per kilogram of reaction mixture at the end of time t, the initial concentration of soluble palladium being shown in the column headed t=0, (*)=mass polymerization of the reaction medium.

EXAMPLES 1 to 8 - Control Experiment (a)

The palladium-containing precursor dissolved in distilled methyl acrylate, tributylphosphonium tetrafluoroborate, and excess tetrafluoroboric acid complexed with ethyl ether were introduced successively into an NSMC stainless steel reactor of capacity 50 cm$^3$ (the concentrations of the different constituents of the catalytic system are expressed in mmol per mole of methyl acrylate charged).

After the reactor was closed and stirring was applied, the temperature of the reaction medium was brought to 110° C.

The course of the reaction was monitored by withdrawing samples with the passage of time and analyzing them by gas chromatography to determine the nature and the proportions of the products formed and by atomic absorption to assay the soluble palladium.

The particular conditions and also the results obtained are reported in the Table below.

triphenylphosphine was added dropwise in the proportion of 17 mmol per mole of methyl acrylate.

After this introduction, the reaction medium was brought to 110° C. and the same determinations were carried out as in Examples 1 to 8.

The results obtained are reported below, using the same conventions as defined above:

|   | RY % | | Soluble [Pd] mmol/kg | |
|---|---|---|---|---|
| t | 2-MEG | DHM | t = 0 | t |

TABLE

| Example No. | [NPBu₃BF₄] mmol/mole NA | Pd(acac)₂ mmol/mole NA | [HBF₄] mmol/mole NA | t | RY % 2-NEG | DNN | soluble [Pd] mmol/kg t = 0 | t |
|---|---|---|---|---|---|---|---|---|
| 1 |  | 0.6 | 2.5 | 35 min | 0.4 | 21 | 6.4 | 6.3 |
|  |  |  |  | 4 hr 25 min | 1.7 | 77 |  | 6.4 |
| 2 | 6 | 1.2 | 2.5 | 55 min | 1.3 | 56 | 13.6 | 13.7 |
|  |  |  |  | 3 hr 55 min | 2 | 85 |  | 13.4 |
| 3 |  | 0.3 | 2.4 | 55 min | 0.3 | 6 | 3.8 | 3.7 |
|  |  |  |  | 6 hr 15 min | 0.5 | 24 |  | 3.6 |
| a | 30 | 0.6 | 0 |  | (*) | (*) |  |  |
| 4 | 32.7 | 0.65 | 2 | 55 min |  | 2 | 6.8 | 6.6 |
|  |  |  |  | 7 hr 20 min | 0.6 | 22.5 |  | 6.1 |
| 5 | 30 | 0.6 | 3.6 | 55 min | 0.5 | 24.5 | 6.4 | 5.6 |
|  |  |  |  | 7 hr 25 min | 1.4 | 60.5 |  | 5.6 |
| 6 | 30.5 | 0.4 | 6 | 55 min | 0.3 | 19 | 6.4 | 3.9 |
|  |  |  |  | 6 hr 25 min | 1 | 41 |  | 4.3 |
| 7 | 42.6 | 0.57 | 2.3 | 55 min | 0.2 | 9 | 5.8 | 5.8 |
|  |  |  |  | 7 hr 25 min | 1.2 | 40.5 |  | 5.9 |
| 8 | 62 | 0.62 | 2.5 | 60 min | 0.1 | 3.2 | 5.9 | 6.0 |
|  |  |  |  | 4 hr 25 min | 0.7 | 16 |  | 5.9 |

EXAMPLE 9

The reactor described above was charged with the following materials according to a procedure similar to that of the above examples:

(i) methyl acrylate;

(ii) palladium acetyl acetonate in the proportion of 0.3 mmol per mole of methyl acrylate;

(iii) tributylphosphonium tetrafluoroborate in the proportion of 31.6 mmol per mole of methyl acrylate; and (iv) tetrafluoroboric acid complexed with ethyl ether, in the proportion of 12.6 mmol per mole of methyl acrylate.

The reaction temperature was 130° C. The results obtained are reported below, using the same conventions as defined above:

|   | RY % | | Soluble [Pd] mmol/kg | |
|---|---|---|---|---|
| t | 2-MEG | DHM | t = 0 | t |
| 50 mn | 0.2 | 6.2 | 7.4 | 7.4 |
| 380 mn | 1.8 | 72 | 7.4 | 7.2 |

EXAMPLE 10

The procedure described in Examples 1 to 8 hereinbefore was modified in that the following materials were introduced successively:

(i) methyl acrylate (279 mmol);

(ii) palladium acetylacetonate in the proportion of 0.68 mmol per mole of methylacrylate and (iii) tetrafluoroboric acid complexed with ethyl ether, in the proportion of 19.7 mmol per mole of methyl acrylate, and in that the reactants were cooled and then

| 85 mn | 0.6 | 23.8 | 3.2 | 3.3 |
|---|---|---|---|---|
| 385 mn | 1.7 | 53.5 | 3.2 | 3 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an alkyl diester, comprising catalytically dimerizing at least one lower alkyl acrylate in the presence of a catalytically effective amount of palladium, tetrafluoroboric acid and a hydrogenophosphonium tetrafluoroborate, and wherein the palladium concentration ranges from 0.1 to 3 mmol per mole of said at least one alkyl acrylate, the reaction temperature ranges from 70° to 150° C. and the hydrogenophosphonium tetrafluoroborate concentration is at least 6 mmol per mole of said at least one alkyl acrylate.

2. The process as defined by claim 1, said hydrogenophosphonium tetrafluoroborate having the formula (IV):

$$(HPR_1R_2R_3)^+BF_4 \qquad (IV)$$

in which $R_1$, $R_2$ and $R_3$ are each an alkyl, cycloalkyl, aryl, alkoxy, cycloalkoxy or aryloxy radical, with the proviso that one of the radicals $R_1$, $R_2$ or $R_3$ may also be a monovalent radical of the formula (II):

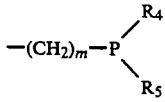 (II)

in which m is an integer ranging from 1 to 4, and $R_4$ and $R_5$ are each an alkyl, cycloalkyl, aryl, alkoxy or aryloxy radical.

3. The process as defined by claim 2, wherein the tetrafluoroborate of formula (IV), $R_1$, $R_2$ and $R_3$, which may be identical or different, are each:

(i) an alkyl radical containing at most 8 carbon atoms;

(ii) a cycloalkyl radical containing from 5 to 7 carbon atoms;

(iii) an aryl radical containing from 6 to 12 carbon atoms;

(iv) an alkoxy radical containing at most 8 carbon atoms; or (v) an aryloxy radical containing from 6 to 12 carbon atoms.

4. The process as defined by claim 1, wherein the palladium concentration ranges from 0.2 to 1.5 mmol per mole of alkyl acrylate.

5. The process as defined by claim 1, wherein the reaction temperature ranges from 90° to 130° C.

6. The process as defined by claim 1, wherein the hydroqenophosphonium tetrafluoroborate concentration ranges from 10 to 100 mmol per mole of alkyl acrylate.

7. The process as defined by claim 1, wherein the amount of fluoroboric acid ranges from 0.5 to 50 mmol per mole of alkyl acrylate.

8. The process as defined by claim 7, wherein the amount of fluoroboric acid ranges from 2 to 15 mmol per mole of alkyl acrylate.

9. The process as defined by claim 1, said hydrogenophosphonium tetrafluoroborate comprising tributylphosphonium tetrafluoroborate.

10. The process as defined by claim 1, said at least one lower alkyl acrylate is methyl acrylate.

* * * * *